(12) United States Patent
Downey et al.

(10) Patent No.: US 12,072,146 B2
(45) Date of Patent: Aug. 27, 2024

(54) SINGLE-USE SPRAY DRYING COMPONENTS AND METHODS OF USING THE SAME

(71) Applicant: Capsugel Belgium NV, Bornem (BE)

(72) Inventors: Brandon J. Downey, Bend, OR (US); Anthony Quach, Bend, OR (US); Dave Hansen, Bend, OR (US); Travis L. Harrer, Bend, OR (US); John Michael Baumann, Bend, OR (US)

(73) Assignee: Capsugel Belgium NV (BE)

( * ) Notice: Subject to any disclaimer, the term of this patent is extended or adjusted under 35 U.S.C. 154(b) by 0 days.

(21) Appl. No.: 18/177,675

(22) Filed: Mar. 2, 2023

(65) Prior Publication Data

US 2023/0213280 A1 Jul. 6, 2023

Related U.S. Application Data

(63) Continuation of application No. 16/640,720, filed as application No. PCT/EP2018/073140 on Aug. 28, 2018, now Pat. No. 11,619,445.

(60) Provisional application No. 62/553,046, filed on Aug. 31, 2017.

(51) Int. Cl.
| | | |
|---|---|---|
| *F26B 3/12* | (2006.01) | |
| *B01D 1/18* | (2006.01) | |
| *B05B 7/16* | (2006.01) | |
| *B05B 15/40* | (2018.01) | |
| *F26B 25/14* | (2006.01) | |
| *F26B 25/16* | (2006.01) | |

(52) U.S. Cl.
CPC .................. *F26B 3/12* (2013.01); *B01D 1/18* (2013.01); *B05B 7/1686* (2013.01); *B05B 15/40* (2018.02); *F26B 25/14* (2013.01); *F26B 25/16* (2013.01)

(58) Field of Classification Search
CPC . F26B 3/12; F26B 25/14; F26B 25/16; B01D 1/18; B05B 7/1686; B05B 15/40
See application file for complete search history.

(56) References Cited

U.S. PATENT DOCUMENTS

| | | |
|---|---|---|
| 4,789,532 A | 12/1988 | Jons et al. |
| 4,809,442 A | 3/1989 | Iwaya et al. |
| 5,869,542 A | 2/1999 | Davies et al. |
| 6,011,089 A | 1/2000 | Davies et al. |
| 6,307,012 B1 | 10/2001 | Davies et al. |

(Continued)

FOREIGN PATENT DOCUMENTS

| | | |
|---|---|---|
| CA | 2 911 788 A1 | 6/2016 |
| CN | 202675818 U | 1/2013 |

(Continued)

OTHER PUBLICATIONS

International Search Report and Written Opinion, mailed Nov. 9, 2018, for International Patent Application No. PCT/EP2018/073140, 13 pages.

*Primary Examiner* — Jessica Yuen
(74) *Attorney, Agent, or Firm* — Klarquist Sparkman, LLP

(57) ABSTRACT

Spray drying method and systems are disclosed that include one or more single-use components. Single-use spray drying systems can include a drying chamber with an inner surface formed of a polymeric material. The single-use components can be pre-sterilized and sterile packaged to provide improved efficiencies and greater operational flexibility in spray drying systems.

10 Claims, 9 Drawing Sheets

FIG. 1

(56) References Cited

U.S. PATENT DOCUMENTS

| | | |
|---|---|---|
| 8,407,912 B2 | 4/2013 | Hubbard, Jr. et al. |
| 8,434,242 B2 | 5/2013 | Hubbard et al. |
| 2011/0142885 A1 | 6/2011 | Haley et al. |
| 2012/0167410 A1 | 7/2012 | Abate et al. |
| 2013/0056158 A1 | 9/2013 | Hubbard, Jr. et al. |
| 2013/0243877 A1 | 9/2013 | Haley et al. |
| 2014/0083627 A1 | 3/2014 | Khan et al. |
| 2014/0083628 A1 | 3/2014 | Khan et al. |
| 2014/0088768 A1 | 3/2014 | Haley et al. |
| 2016/0084572 A1 | 3/2016 | Khan et al. |
| 2016/0353773 A1 * | 12/2016 | Weissbrodt ............. A23L 27/10 |

FOREIGN PATENT DOCUMENTS

| | | | |
|---|---|---|---|
| CN | 103037946 A | 4/2013 | |
| CN | 103653106 A | 3/2014 | |
| CN | 105168274 A | 12/2015 | |
| CN | 105413207 A | 3/2016 | |
| EP | 3 059 537 A1 | 8/2016 | |
| GB | 2531009 A | 4/2016 | |
| JP | 2008-182911 A | 8/2008 | |
| WO | WO 2001/033971 A1 | 5/2001 | |
| WO | WO-2010000941 A1 * | 1/2010 | ............ B29C 53/62 |
| WO | WO 2012/058575 A2 | 5/2012 | |
| WO | WO 2017/079468 A1 | 5/2017 | |

\* cited by examiner

SINGLE-USE SPRAY DRYING COMPONENTS AND METHODS OF USING THE SAME

CROSS REFERENCE TO RELATED APPLICATIONS

This is a continuation of U.S. patent application Ser. No. 16/640,720, filed Feb. 20, 2020, which is the U.S. National Stage of International Application No. PCT/EP2018/073140, filed Aug. 28, 2018, which was published in English under PCT Article 21(2), which in turn claims the benefit of U.S. Provisional Application No. 62/553,046, filed Aug. 31, 2017. The prior applications are incorporated herein by reference in their entirety.

FIELD

The present application relates to single-use spray drying components and methods for using the same.

BACKGROUND

As the pharmaceutical industry moves towards manufacturing increasingly diverse medicines, including, for example, small-volume, highly potent compounds for niche markets, there remains a need to provide shelf-stable, dry powder formulations of these medicines.

Spray drying can be used to produce thermostable powders, including those that can be reconstituted for point of care use. However, manufacturing medicines by spray drying can be complex, time-consuming, and expensive because of the generally inflexible nature of a regulated manufacturing environment, which often requires highly specialized processing equipment and containment technologies. Costs can be particularly high when manufacturing clinical or other small batch supplies of these medicines, or when manufacturing highly-potent or sterile medicines that require even more stringent processing conditions. Development of cleaning protocols and procedures to reduce risk of batch carryover or contamination can also constitute a significant cost and time investment.

Improvements in spray drying systems that provide greater operational flexibility, reduce costs, or otherwise increase the efficiency of manufacturing processes are desirable for manufacturing medicines or other compounds suitable for spray drying.

SUMMARY

Apparatuses and methods of spray drying with single-use components, such as drying chambers or portions thereof, are disclosed herein.

In one embodiment, a method of spray drying using a single-use drying chamber with an inner surface that comprises a polymeric material is provided. The method includes securing the single-use drying chamber to a laterally-extending spacing member of a gas inlet manifold to establish a gap between an inner surface of an inlet end of the single-use drying chamber and an outer surface of the gas passageway. A spray liquid can be directed through a spray liquid passageway to an atomizer positioned adjacent the gas outlet, forming a plurality of droplets that are directed into the single-use drying chamber. A drying gas can be introduced through the gas passageway and out the gas outlet into the single-use drying chamber to at least partially dry the plurality of droplets and form a plurality of spray-dried particles, and the spray-dried particles can be directed out the single-use drying chamber.

In some embodiments, the spacing member can extend sufficiently from an exterior surface of the gas passageway to establish a gap (e.g., a circumferential gap) between the inner surface of the inlet end of the drying chamber to the outside surface of the gas passageway of a length that is greater than 50% and less than 200% of a radius of the gas passageway.

In some embodiments, the drying gas can be introduced into the single-use drying chamber at a temperature greater than 100° C., greater than 150° C., or greater than 200° ° C. In some embodiments, the drying gas can be introduced into the single-use drying chamber at a temperature of less than 250° C.

The polymeric material can comprise any material suitable for containing product during a spray drying process. In some embodiments, polymeric material can be a thermoplastic material. In other embodiments, the polymeric material comprises, or alternatively consists of, a material selected from one of LDPE, HDPE, PET, BoPET, PETE, Polystyrene, PVC, PES, PSU, PC, PA, and PBT.

The polymeric material can be a flexible material and, in some embodiments, the introduction of the drying gas into the single-use drying chamber inflates the flexible, single-use drying chamber to define an enclosed volume.

The heat-sensitive material can form an inner layer of the drying chamber and, in some embodiments one or more outer layers can at least partially surround the inner layer. The outer layer can be formed of a different material from the first layer.

In some embodiments, the drying chamber can be pre-sterilized, such as by gamma radiation.

In another embodiment, a spray drying apparatus is provided with a gas inlet manifold and a single-use drying chamber. The manifold has a gas passageway and a spacing member that extends laterally from the gas passageway of the gas inlet manifold and the drying chamber has a first opening defined by a first surface portion at an inlet end, a second opening defined by a second surface portion at an outlet end, and a third surface portion extending longitudinally from the inlet end to the outlet end. An atomizer is provided at a distal end of a spray liquid inlet pipe, and the first surface portion is coupled to the spacing member at a location that is spaced apart from the gas passageway by a distance greater than 50%, 75%, 100%, or 125% of a radius of the gas passageway. In some embodiments, the distal end of the spray liquid inlet pipe extends into the single-use drying chamber.

In some embodiments, the drying chamber can have an inner layer and an outer layer. The inner layer can be formed from a flexible material that can inflate from a collapsed configuration to an expanded configuration. The outer layer can have a larger size than the outer layer. For example, the first layer can have a larger diameter taken at a midpoint between the inlet end and the outlet end in a fully-expanded configuration than a second diameter of the outer layer at the same location.

In another embodiment, a spray drying method includes directing a spray liquid through a first passageway to an atomizer positioned adjacent a gas outlet, the first passageway including a proximal portion coupled to an spray liquid reservoir and a distal portion coupled to the atomizer, forming a plurality of droplets using the atomizer and directing the plurality of droplets into a drying chamber with an inner surface comprising a polymeric material, and introducing a drying gas through a gas passageway and into the drying chamber to at least partially dry the plurality of droplets and form a plurality of spray-dried particles. The gas passageway can have an outer wall that is spaced from a first surface that defines an opening in an inlet end of the drying chamber and the drying gas can be at a temperature of between 130° C. and 250° C. as it exits the gas passageway and enters the drying chamber.

In some embodiments, a temperature of the drying gas, as measured at the first, opening-defining surface, does not exceed a temperature of the drying gas as it exits the drying chamber.

In some embodiments, an outlet relative humidity of the spray-dried particles (e.g., the product) can be less than 12%, or between 2% and 10%. In another embodiment, a liquid to gas ratio during operation can be between 0.015 and 0.03 on a mass basis.

The spray liquid can comprise an active pharmaceutical ingredient and/or other components (e.g., food or nutritional components).

In another embodiment, a method of producing spray-dried particles comprises atomizing a first spray liquid in a drying chamber comprising an first inner surface formed of a first polymeric material, introducing a drying gas into the drying chamber to at least partially dry the atomized first spray liquid and form a plurality of first spray-dried particles, collecting the first spray-dried particles, removing the first inner surface, replacing the first inner surface with a second inner surface formed of a second polymeric material (either the same as or different from the first polymeric material), atomizing a second spray liquid in the drying chamber, introducing a drying gas into the drying chamber to at least partially dry the atomized second spray liquid and form a plurality of second spray-dried particles, and collecting the plurality of second spray-dried particles.

In some embodiments, the drying chamber comprises an outer layer that at least partially surrounds the inner surface and the act of removing the first inner surface comprises moving the inner surface away from the outer layer and withdrawing the first inner surface from the drying chamber.

In other embodiments, the first inner surface is secured to a spacing member of an inlet manifold, and the act of removing the first inner surface comprises removing the first inner surface from the spacing member and the act of replacing the first inner surface with a second inner surface comprises securing the second inner surface to the spacing member. The first inner surface and second inner surface can also be pre-sterilized by gamma irradiation.

In other embodiments, the act of replacing the first inner surface with a second inner surface is performed when the second spray liquid is different from the first spray liquid, after either a predetermined number of spray drying operations with the first inner surface, or after a predetermined amount of time of spray drying operation with the first inner surface. The act of replacing the first inner surface with a second inner surface can be performed in lieu of heat sterilizing the drying chamber.

In another embodiment, all of the components in the product flow path, including the inner surface of the drying chamber can be removed and replaced in lieu of heat sterilization.

In another embodiment, a method of spray drying includes providing a plurality of first pre-sterilized components associated with a product flow path of a first spray drying process, removing the plurality of first pre-sterilized components from sterile packaging, installing the plurality of first pre-sterilized components in a spray drying system, performing a first spray drying process in which the plurality of first pre-sterilized components are exposed to one or both of a first spray liquid or first spray-dried product in the product flow path, removing the plurality of first pre-sterilized components, providing a plurality of second pre-sterilized components of the product flow path, removing the plurality of second pre-sterilized components from sterile packaging, installing the plurality of second pre-sterilized components in the spray drying system, and performing a second spray drying process in which the plurality of second pre-sterilized components are exposed to one or both of a second spray liquid or second spray-dried product in the product flow path.

In some embodiments, the plurality of pre-sterilized components comprise a drying chamber. In other embodiments, the plurality of first pre-sterilized components comprise one or more of a gas inlet filter, inlet manifold, nozzle wand, spray liquid filter, product-contact drying chamber (e.g., an inner layer of a drying chamber), a collection cone, a cyclone, and a production collection container, and a gas outlet filter.

It is to be understood that both the foregoing general description and the following detailed description are exemplary and explanatory only and are not restrictive of the claimed subject matter.

DETAILED DESCRIPTION

Figure 1:
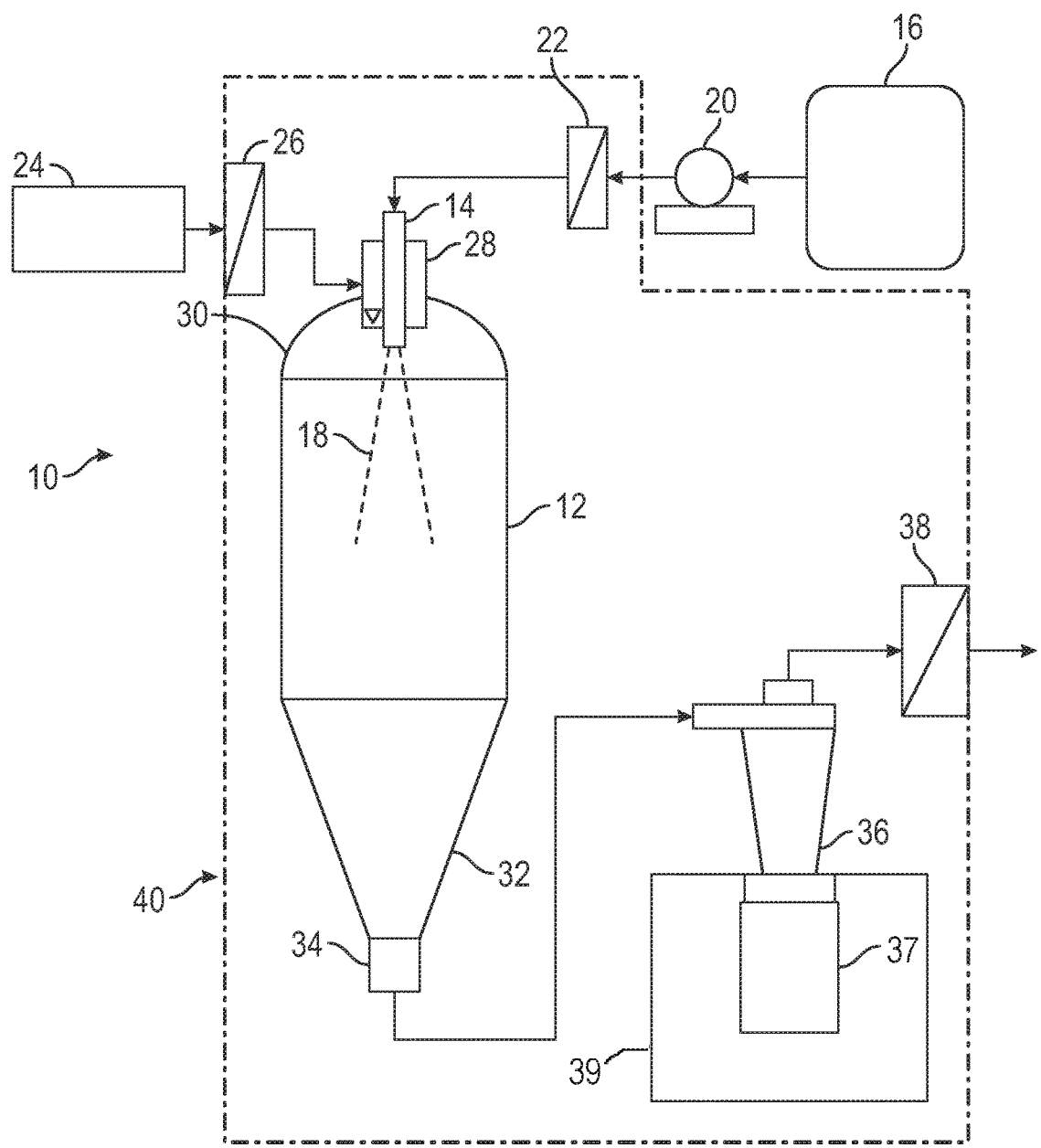
FIG. 1 is a schematic view of a spray drying system.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

Definitions

The explanations of terms and abbreviations herein are provided to better describe the present disclosure and to guide those of ordinary skill in the art in the practice of the present disclosure.

As used herein, the term "and/or" used between the last two of a list of elements means any one or more of the listed elements. For example, the phrase "A, B, and/or C" means "A," "B," "C," "A and B," "A and C," "B and C," or "A, B, and C."

As used herein, the term "coupled" generally means physically coupled or linked and does not exclude the presence of intermediate elements between the coupled items absent specific contrary language.

As used herein, reference to an element by the indefinite article "a" or "an" does not exclude the possibility that more than one of the element is present, unless the context clearly requires that there is one and only one of the elements. The indefinite article "a" or "an" thus usually means "at least one." The disclosure of numerical ranges should be understood as referring to each discrete point within the range, inclusive of endpoints, unless otherwise noted. The term "about" as used in the disclosure of numerical ranges indicates that deviation from the stated value is acceptable to the extent that the deviation is the result of measurement variability and/or yields a product of the same or similar properties.

As used herein, the term "spray drying" refers to processes involving breaking up liquid mixtures into small droplets (atomization) and rapidly removing solvent from the mixture in a container (drying chamber) where there is a strong driving force for evaporation of solvent from the droplets. The strong driving force for solvent evaporation is generally provided by maintaining the partial pressure of solvent in the spray-drying apparatus well below the vapor pressure of the solvent at the temperature of the drying droplets. This can be accomplished by (1) mixing the liquid droplets with a warm drying gas, (2) maintaining the pressure in the spray-drying apparatus at a partial vacuum (e.g., 0.01 atm to 0.50 atm), or (3) both. Generally, the temperature and flow rate of the drying gas is chosen so that the droplets of the spray liquid are dry enough by the time they reach the wall of the apparatus that they are essentially solid, form a fine powder, and do not stick to the apparatus wall. The actual length of time to achieve this level of dryness depends on the size of the droplets and the conditions at which the process is operated. Droplet sizes may range from 1 μm to 500 μm in diameter, the size being dependent on the desired particle size of the spray dried powder. The large surface-to-volume ratio of the droplets and the large driving force for evaporation of solvent lead to actual drying times of a few seconds or less, and often less than 0.1 second. Solidification times should be less than 100 seconds, and often less than a few seconds.

As used herein, the term "single-use" refers to a component of a spray drying system that is used by the system in one type of spray-drying process, and then removed from the system and replaced with another unused, single-use component when a different type of spray drying process is to be performed by the system. Thus, single-use components are not subjected to in-place sterilization. For example, a single-use drying chamber is a drying chamber that is used for a first spray drying process and then replaced by another unused, single-use drying chamber before beginning a second spray drying process. However, a single-use drying chamber can, in some cases, be reused in subsequent processes that produce the same material as the first process. A single-use component can be disposable (e.g., destroyed or otherwise disposed of) or recyclable (sterilized for reuse or recycled for materials in whole or in part) after use.

As used herein, the term "pre-sterilized" refers to a component that is sterilized and provided for use in a packaged condition that effectively maintains the sterility of the component. As used herein, the term "sterile packaging" refers to the packaging that effectively maintains the sterility of the pre-sterilized component. At the time of use, a pre-sterilized component is removed from its sterile packaging prior to installation and use. Pre-sterilized components that are sterile packaged need not be subjected to installation sterilization since they are ready for use in a sterilized condition.

As used herein, the term "product" refers to the product, such as a powder, of a spray drying process in which a liquid has been at least partially dehydrated.

As used herein, the terms "heat sterilization" or "heat sterilized" refers to a sterilization process that uses heat at temperatures of 100° C. or more (with or without water vapor or other gases) to sterilize a surface of a component.

As used herein, the term "in-place sterilization" refers to a sterilization and/or cleaning process that is performed on a component of a spray drying system that has been in contact with a spray liquid or spray-dried product so that the component can be used again, without replacement, to spray dry a different product. In-place sterilization is performed during product changeovers in order to reduce or eliminate the risk of cross-contamination. In-place sterilization can include heat sterilization.

As used herein, the term "installation sterilization" refers to a sterilization and/or cleaning process that is performed on a component of a spray drying system after it has been installed. Installation sterilization can be performed to provide sterile surfaces suitable for product contact during a subsequent spray drying process with the installed component. Installation sterilization can include heat sterilization.

As used herein, the term "spray liquid" means a composition that includes a material that is desired to be spray dried. The spray liquid can include, for example, mixtures, emulsions, solutions, suspensions, and/or combinations thereof.

As used herein, the term "product flow path" refers to a flow path of the spray liquid and resulting product through the spray drying system.

As used herein, the term "polymeric material" refers to any natural or synthetic polymeric material.

As used herein, a "heat-sensitive material" is a material that has a melting point of 300° C. or less.

Single-Use Drying Chambers

Due to the risks of product contamination, conventional pharmaceutical dryers can be difficult to validate for high containment of high potency medicines (particularly during product changeovers), and extremely difficult to validate for aseptic processing. This lack of containment means that the entire manufacturing area must be thoroughly cleaned and validated between each product campaign. Trace amounts of product can remain, and, especially in the case of highly-potent compounds, product integrity (and, in some cases, product safety) of later runs can be compromised.

The use of single-use drying chambers and other single-use components in the product flow path greatly reduce the risk of cross-contamination. In addition, batch cycle time can be reduced by providing sterile conditions for spray drying, while reducing and/or eliminating the need for the complex and time-consuming sterilization procedures during product changeovers. Thus, for example, after spray drying is completed, the single-use drying chambers disclosed herein can be replaced with a new (e.g., unused) single-use drying chamber. In addition, to further decrease the time required for product changeovers, the single-use drying chambers disclosed herein can be pre-sterilized and sterile packaged so that they are ready to use whenever needed.

As described in more detail below, the single-use drying chamber can be formed of a single layer or, alternatively, the single-use drying chamber can comprise an inner layer and one or more outer layers. The inner layer (whether used with other layers or not) can be formed of any material suitable to completely contain the resulting product (e.g., powder).

In some embodiments, the inner layer can be selected from a material that is impermeable to the product that is being produced by the spray drying procedure. In a preferred embodiment, the gas permeation coefficient of the inner layer can be <50,000 barrer (10-10 cm$^3$ (STP)·cm/cm$^2$·s·cm-Hg) for Nitrogen. By way of comparison, LDPE has a gas permeability of 1.9 barrer and silicone has a gas permeability of 36,000 barrer.

In some embodiments, the inner layer can be selected to a have a relatively low thickness, which can advantageously reduce the amount of material required for the inner layer. For example, the inner layer can have a thickness of 0.05 mm to 1.0 mm in some embodiments, a thickness of 0.1 mm to 0.5 mm in other embodiments, and a thickness of 0.1 to 0.3 mm in still other embodiments.

In embodiments that use an outer layer, the outer layer does not contact the product because the product is fully contained by the inner layer. Thus, the outer layer can be formed of various materials, and the outer layer can be disposable or reuseable since the outer layer may not require sterilization (or require only minor sterilization) between operations.

The outer layer can be formed of a rigid material, such as a rigid plastic or conventional stainless steel drying chamber, or a flexible material, such as a flexible plastic or other non-rigid material). Thus, for example, a single-use, pre-sterilized layer positioned within a conventional stainless steel drying chamber provides a sterile containment for product that reduces or eliminates the need to separately sterilize the surface of the stainless steel drying chamber.

In some embodiments, the single-use drying chamber can have an inner surface that is formed of a polymer. The polymer can comprise, for example, a plastic. In some embodiments, the inner surface can comprise a plastic film. For example, the inner surface of the drying chamber can comprise, or alternatively consist of, one or more of the following materials: LDPE, HDPE, PET, BoPET, PETE, Polystyrene, PVC, PES, PSU, PC, PA, PBT, combinations thereof, or films of other similar materials capable of containing pressurized gas.

In some embodiments, the material of the inner layer can be flexible material, such as a flexible film. As discussed above, for spray drying pharmaceuticals and other materials that require sterile environments, the material preferably has physical properties and characteristics that are suitable for product contact. For example, in one embodiment, the inner layer can comprise low-density polyethylene (LDPE), which has a low risk for leachables/extractables when exposed to at least some of the temperatures disclosed herein.

In some embodiments, the single-use drying chamber can have an inner surface formed of a heat-sensitive material that has a melting point of 300° C. or less. In other embodiments, the material of the inner surface can have a melting point of 250° C. or less, 225° C. or less, or 200° ° C. or less.

FIG. 1 illustrates a spray-drying apparatus 10 that includes a drying chamber 12, an atomizer 14, and a reservoir 16. The spray liquid is delivered from reservoir 16 (e.g., a tank) to atomizer 14, where it is sprayed as droplets 18 into drying chamber 12. A pump 20 can be provided to cause the spray liquid to move from the reservoir 16, through an optional sterile filter 22, to atomizer 16 for delivery into drying chamber 12.

The spray liquid can comprise various components, including, in some embodiments, one or more active agents (e.g., active pharmaceutical ingredients or other agents that exert a desired physiological effect on a mammal, including, but not limited to humans). In some embodiments, the spray liquid can comprise a solute that comprises at least one active agent. In one embodiment, the active agent can be dissolved in a solvent. In another embodiment, a portion of the active agent can be suspended or not dissolved in a solvent. In another embodiment, the active agent can be dissolved in the solvent, while a portion of an excipient (or one or more excipients) is dissolved in the solvent.

A drying gas can be delivered from a gas source 24, through an optional filter 26, to a gas inlet manifold 28 and into drying chamber 12. Drying chamber 12 has an inlet end 30 and an outlet end 32. Drying chamber 12 is coupled to gas inlet manifold 28 at inlet end 30, and coupled to a collection member 34 (e.g., a rigid collection cone) at outlet end 32. The drying gas mixes with droplets 18, causing a portion of the mixture (e.g., the solvent) to evaporate from the droplets to produce a powder. Powder (e.g., the spray-dried solute) then exits drying chamber 12 at outlet end 32. After exiting drying chamber 12, the powder is separated and removed from the exiting exhaust gas. The separation of the powder from the exiting exhaust gas can be achieved by various means, such as a cyclone 36. The powder is then collected in one or more product collection container 37. Exhaust gas exiting the cyclone 36 can be directed through one or more outlet filters 38.

Drying gas can be any suitable gas for facilitating the evaporation of the solvent from the droplets. In some embodiments, the drying gas can be an inert gas such as nitrogen, nitrogen-enriched air, or argon to reduce undesirable interactions (e.g., oxidation) with active agents contained in the spray liquid. The temperature of the drying gas at the inlet end 30 of drying chamber 12 (i.e., measured at or near where the gas enters the drying chamber) can be from about 60° ° C. to about 300° C.

A schematic process isolation boundary 40 is shown in FIG. 1. Boundary 40 illustrates one exemplary embodiment of an isolated zone, within which equipment can preferably be sterilized or replaced between uses. As discussed in more detail here, the drying chamber can be a single-use drying chamber, which may be removed and replaced to prevent cross-contamination after use. Other equipment within the isolation boundary, such as the gas inlet manifold and cyclone can also be disposed of and replaced.

Thus, for example, components that are in a product flow path shown in FIG. 1, such as the gas inlet filter 26, inlet manifold 28, atomizer (nozzle wand) 14, solution filter 22, drying chamber 12 (i.e., at least an inner layer), rigid collection cone 34, cyclone 36, gas outlet filter 38, and product collection container 37 can all be isolated from the environment. Each of these components can be pre-sterilized and sterile packaged for use. Thus, after performing a first spray drying operation, all (or some) of these components can be replaced by removing a new, unused component from sterile packaging and installing the new component in place of the used component. In this manner, the sterility of the components in the product flow path is assured without the need for timely and complicated sterilization and validation procedures.

Alternatively, in some embodiments, one or more of the components in the product flow path can be sterilized after completing a first spray drying process to produce a first product and before beginning a second spray drying process to produce a second product that is different from the first.

If desired, one or more disposable isolators, such as inflatable modules, can be provided to further isolate and contain product within the isolation boundary. For example, a product collection disposable isolator 39 is shown in FIG. 1.

In some embodiments, drying chamber 12 is a flexible drying chamber that can inflate upon the introduction of a drying gas into the drying chamber. Upon inflation, the drying chamber defines an enclosed volume of drying chamber 12, which can be maintained throughout a spray drying process.

During a spray drying process, drying gas enters inlet end 30, and the drying gas and entrained particles exit outlet end 32 of drying chamber 12. Inlet end 30 can include an inlet annular connector adapted for connection to the gas inlet manifold 14. Inlet annular connector can define an opening through which the drying gas enters drying chamber 12.

Similarly, outlet end 32 can include an outlet annular connector adapted for connection to collection member 34 (e.g., a rigid collection cone). Outlet annular connector can define an opening through which the drying gas and entrained particles exit the drying chamber.

One or more conductive materials (e.g., a conductive mesh) can be provided in or on drying chamber 12 to ground the system through a conductive member (e.g., conductive clip).

Figure 2:
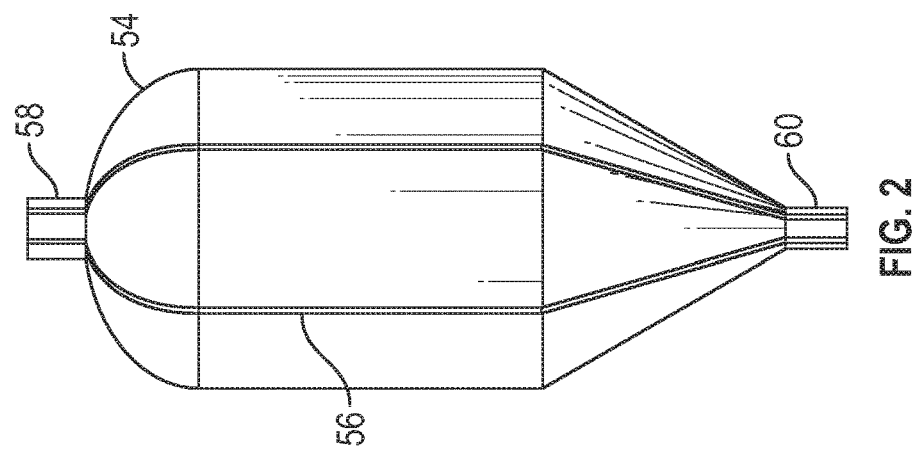
FIG. 2 is a schematic view of a drying chamber.

As shown in FIG. 2, a jacket 54 can optionally be provided to substantially enclose drying chamber 12. Jacket 54 can be positioned and secured (e.g., using zipper 56) over drying chamber 12 to decrease heat loss from drying chamber 12 during a spray drying process. In some embodiments, a first end 58 of jacket 54 can cover portions (or all) of gas inlet manifold 28 and/or a second end 60 of jacket 54 can cover portions (or all) of collection member 34. Where drying chamber 12 can be a single-use drying chamber, jacket 54 is preferably reusable.

Drying chamber 12 has an exterior wall, which defines a chamber volume when the drying chamber is inflated. In one embodiment, as shown in FIG. 1, drying chamber 12 has a top rounded portion, a cylindrical section, and a bottom tapered cone section.

The drying chamber can be made from a material capable of withstanding the elevated pressure and temperature conditions encountered during spray drying. In some embodiments, the material of the drying chamber has a melting point that is below the maximum temperature of the drying gas in the spray drying process, but above a maximum temperature that the material is directly exposed to during the spray drying process, usually the outlet temperature. As discussed below, the drying chamber can be subjected to one or more sterilization processes, other than heat sterilization, before use.

When using materials that have relatively low melting points, such as LDPE which has a melting of about 120° C., the drying chamber can be protected from a heated drying gas as described herein. For example, temperatures of the drying gas entering the drying chamber can exceed (or approach) a melting point of the material of the drying chamber by spacing a top portion of the drying chamber away from the location where the inlet gas enters the drying chamber (i.e., where the drying gas is at its highest temperature). In particular, in some embodiments, a surface that defines an opening of drying chamber at the inlet end can be protected from direct exposure to the heated gas as it is directed into the drying chamber by spacing the surface (and adjacent walls) away from the drying gas as it enters the drying chamber.

In some embodiments, the atomizer can be located adjacent to (i.e., at or next to) an outlet of the drying gas conduit. By locating the atomizer in this manner, the temperature of the drying gas can be reduced sufficiently so that a temperature of the drying gas contacting inner walls of the drying chamber is below the melting point of the material of the drying chamber. For example, an LDPE drying chamber can have an outlet temperature of a drying gas exiting the drying chamber that is less than 120° C.

Since the drying capacity of a spray dryer (or throughput) is dependent on the amount of enthalpy entering the drying chamber in the form of hot drying gas, increasing the inlet temperature of the drying gas above the melting point of a heat-sensitive material of the drying chamber can increase the throughput and/or decrease the residual solvent content of the powder produced. Accordingly, in some embodiments, the temperature of the drying gas at the inlet end of the drying chamber can exceed a melting point temperature of the heat-sensitive material of the drying chamber (e.g., above 120° C. for LDPE).

In embodiments where LDPE or other similar heat-sensitive materials are used, the temperature of the drying gas entering the drying chamber can be between 100° C. and 250° C., between 100° C. and 200° ° C., between 120° ° C. and 250° C., between 150° C. and 250° C., between 120° ° C. and 200° ° C., or between 120° C. and 150° C.

In some embodiments, the temperature of the drying gas at the outlet end of the drying chamber can be 120° C. or less during normal spray conditions (e.g., for LDPE), or otherwise under the temperature of the particular melting point for the selected material of the drying chamber.

Figure 3:
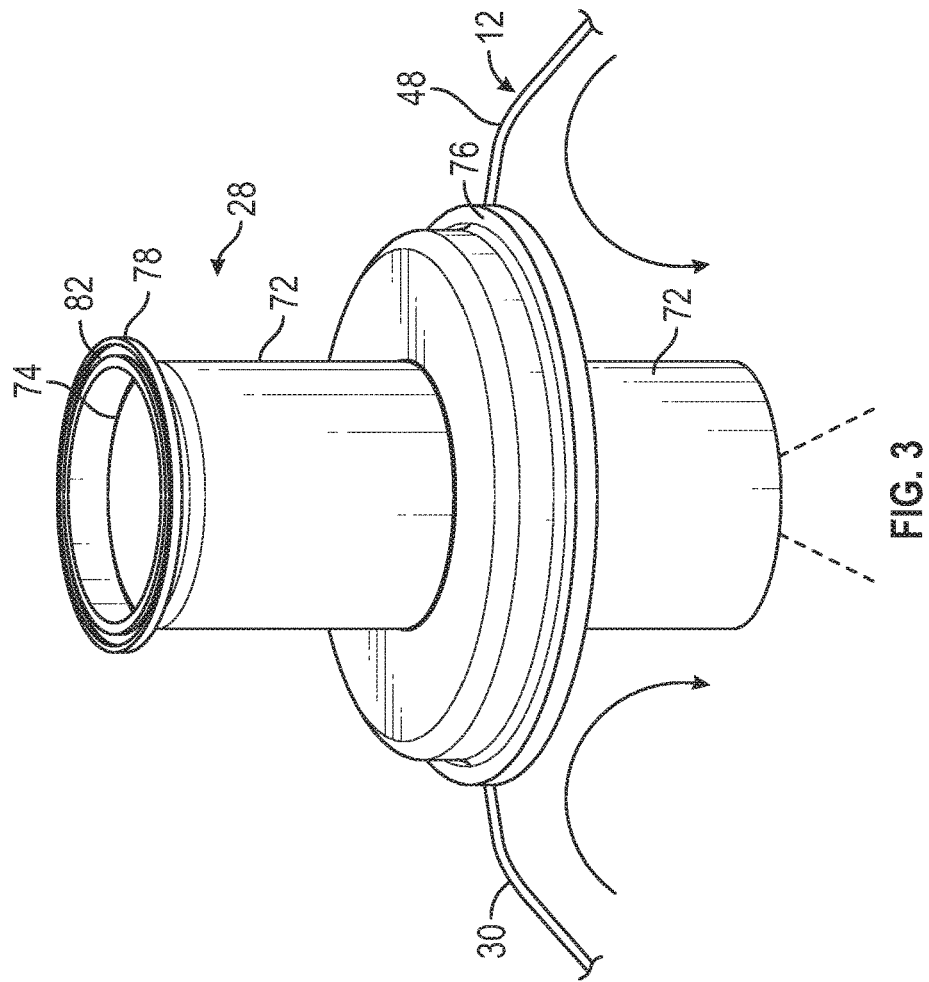
FIG. 3 is a perspective view of a gas inlet manifold coupled to a drying chamber.

Referring now to FIG. 3, a perspective view of a gas inlet manifold 28 is shown. The gas inlet manifold 28 comprises an inlet conduit 72 defining a central opening 74 through which drying gas flows and enters the drying chamber.

As shown in FIG. 3, gas inlet manifold 28 can have a spacing member that protects or shields portions of the inlet end of drying chamber from excessive heat. In one embodiment, the spacing member can be located between a drying chamber surface and the outlet of the drying gas conduit.

The spacing member can comprise an annular flange 76 that extends laterally from gas inlet manifold 28 away from an external wall 86 of inlet conduit 72. Annular flange 76 can be configured to connect to the inlet annular connector 42 of drying chamber 12.

Figure 4:
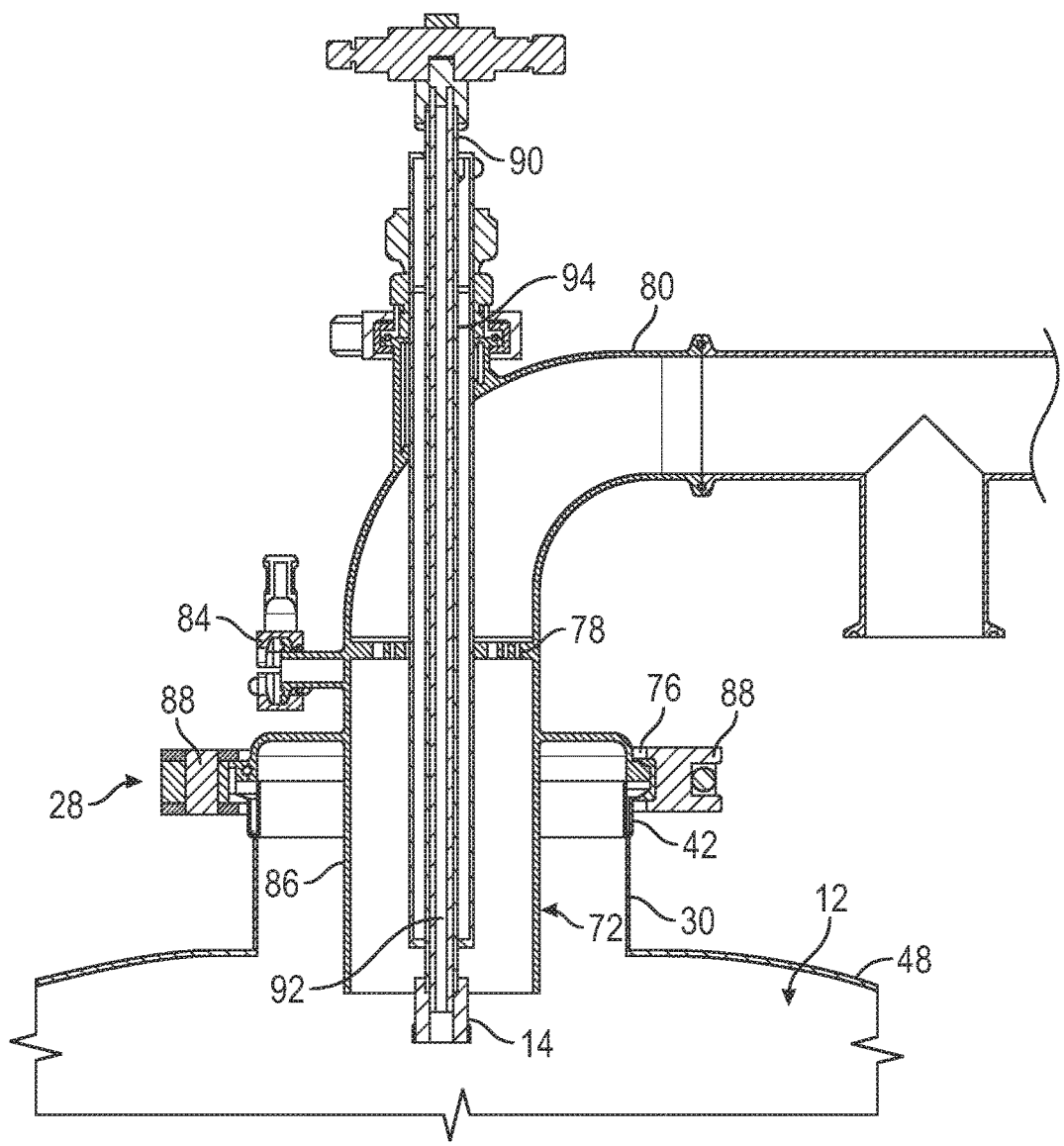
FIG. 4 is a cross-sectional view of an assembled gas inlet manifold, atomizer, and drying gas conduit.

Another coupling member (e.g., flange 78) can be provided at an upper end of gas inlet manifold 28. Flange 78 can be adapted to connect to a drying gas conduit 80 (shown in FIG. 4). Gas inlet manifold 28 can be secured to flange 78 in an air-tight manner. For example, as shown in FIG. 3, a groove 82 in flange 78 can be provided for receiving one or more O-rings to secure, in an air-tight manner, gas inlet manifold 28 to drying gas conduit 80. Alternatively (or in addition), other suitable connections for making an air-tight seal may be used. As shown in FIG. 4, one or more securing mechanism (e.g., first clamp 84) can be provided to secure flange 78 to drying gas conduit 80.

Drying chamber 12 can have an opening defined by a surface though which gas inlet manifold 28 extends and which engages with gas inlet manifold 28. When drying chamber 12 is coupled to gas inlet manifold 28, annular flange 76 spaces the engaging surface (e.g., the circumferential surface of drying chamber 12 shown in FIG. 3) from external wall 86 to reduce an amount of heat transferred from inlet conduit 72 to the external wall 48 of drying chamber 12. Although shown as a generally circular surface, the engaging surface that defines the opening and engages with the gas inlet manifold 28 can have other shapes.

The inlet annular connector 42, which is coupled to the engaging surface that defines the opening in the drying chamber, can be coupled to annular flange 76. Thus, flange 76 shields the engaging surface of the drying chamber by spacing apart the circumferential surface from the gas passageway of the inlet conduit 72 by a distance greater than 50%, greater than 75%, greater than 100%, or, in some embodiments, greater than 125% of a radius of the gas passageway. In some embodiments, the distance the engaging surface of the drying chamber can be spaced apart from the gas passageway is preferably less than 200% of a radius of the gas passageway (e.g., 50-200%, 75-200%, 100-200%, 125-200%). Radius generally refers to half of the length of a circular diameter; however, to the extent that the structure is non-circular in cross section, the term radius refers to half the length of the longest cross-sectional dimension of the component.

Figure 9:
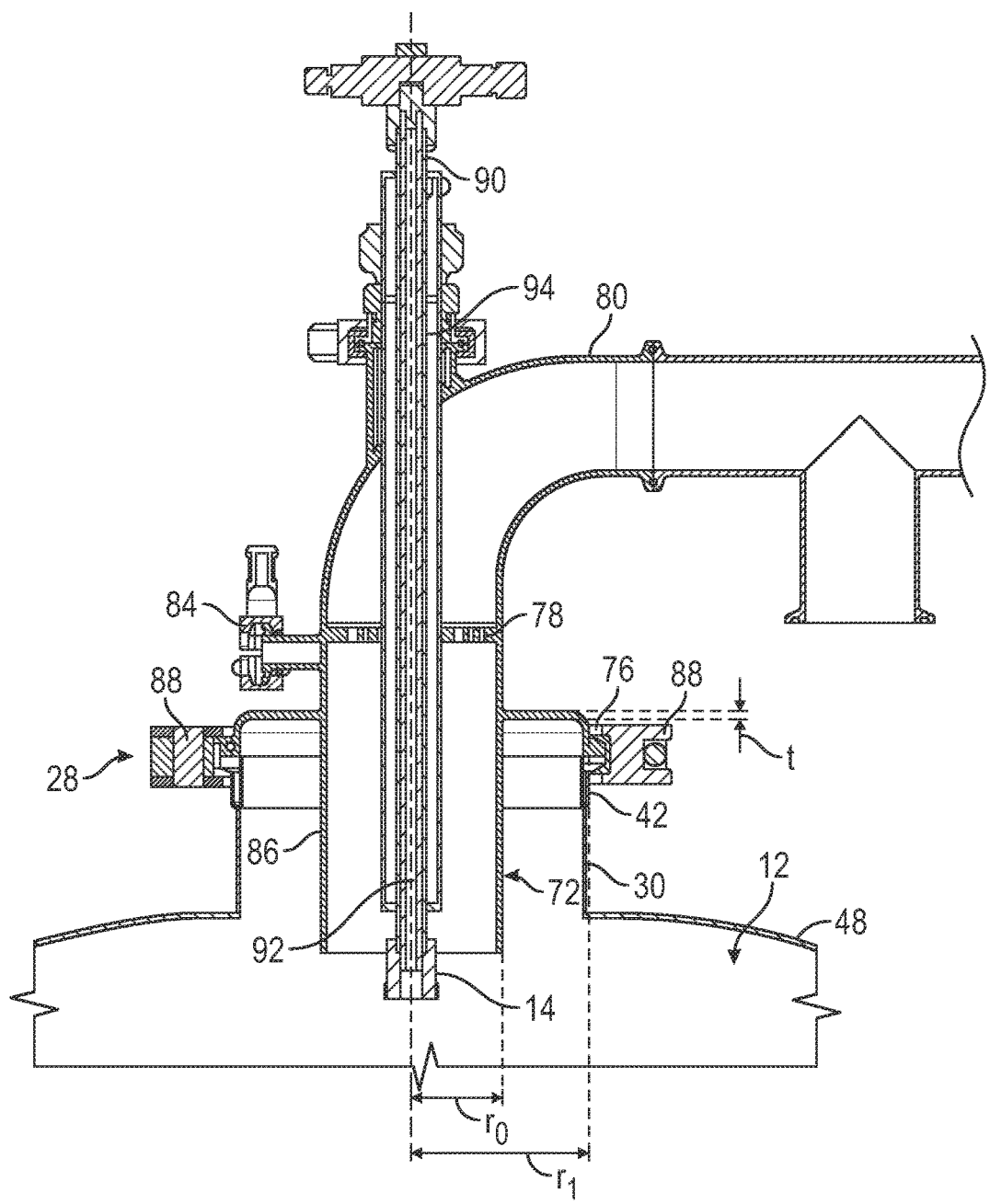
FIG. 9 illustrates the exemplary assembled gas inlet manifold shown in FIG. 5, with additional dimensions identified.

Referring to FIG. 9, for example, a percentage of spacing provided, relative to the radius of the gas passageway r0, can be calculated as ((r1−r0)/r0)×100. Thus, for example, FIG. 9 illustrates an embodiment in which the engaging surface of the drying chamber is spaced apart from the gas passageway of the inlet conduit by a distance of about 100% of the radius of the gas passageway.

The gas inlet manifold, or portions thereof, can be formed of a rigid material that serves to minimize conduction of the inlet heat from the drying gas to portions of the drying chamber in contact with flange 76.

Figure 5:
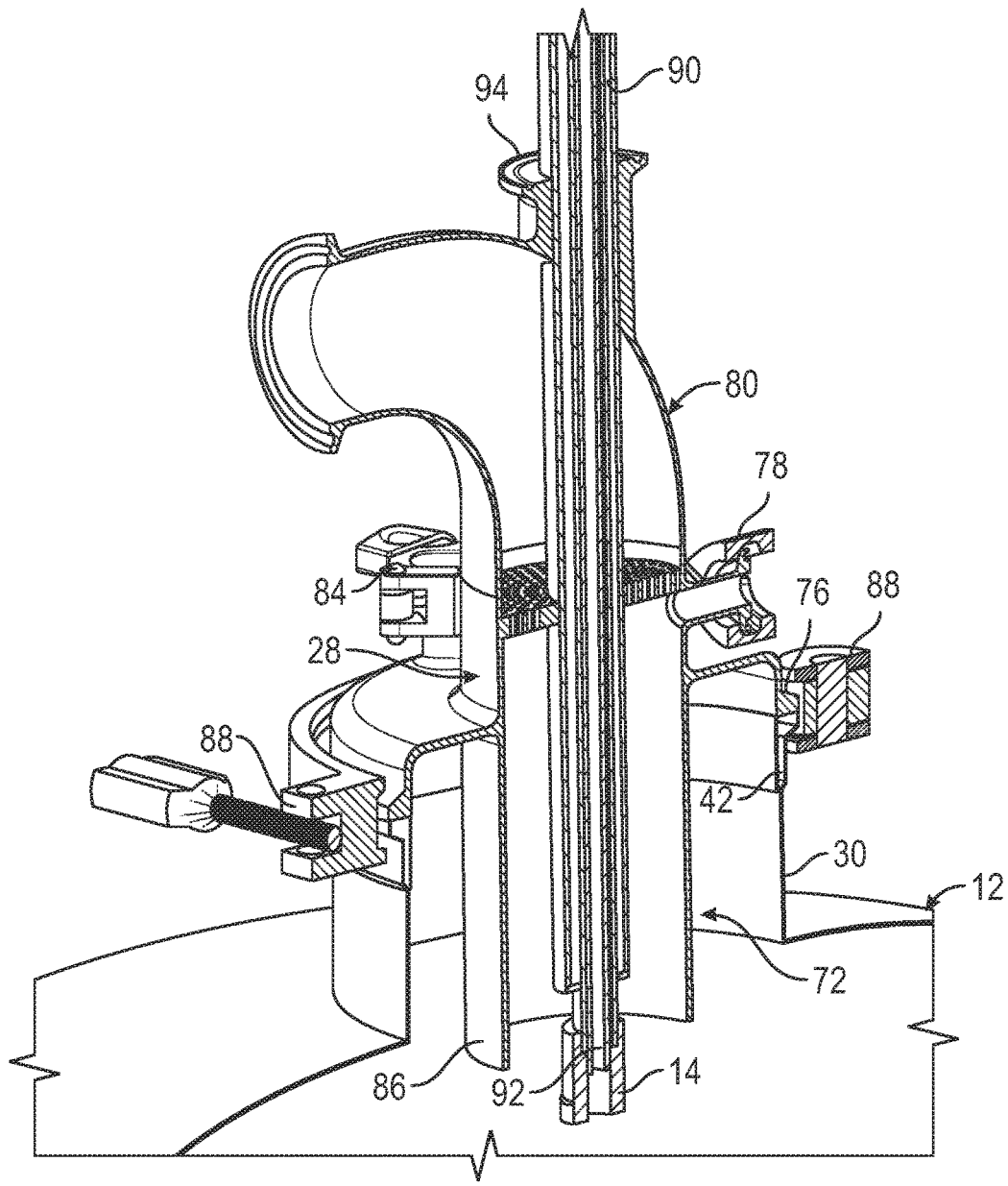
FIG. 5 is another cross-sectional view of an assembled gas inlet manifold, atomizer, and drying gas conduit.
Figure 6:
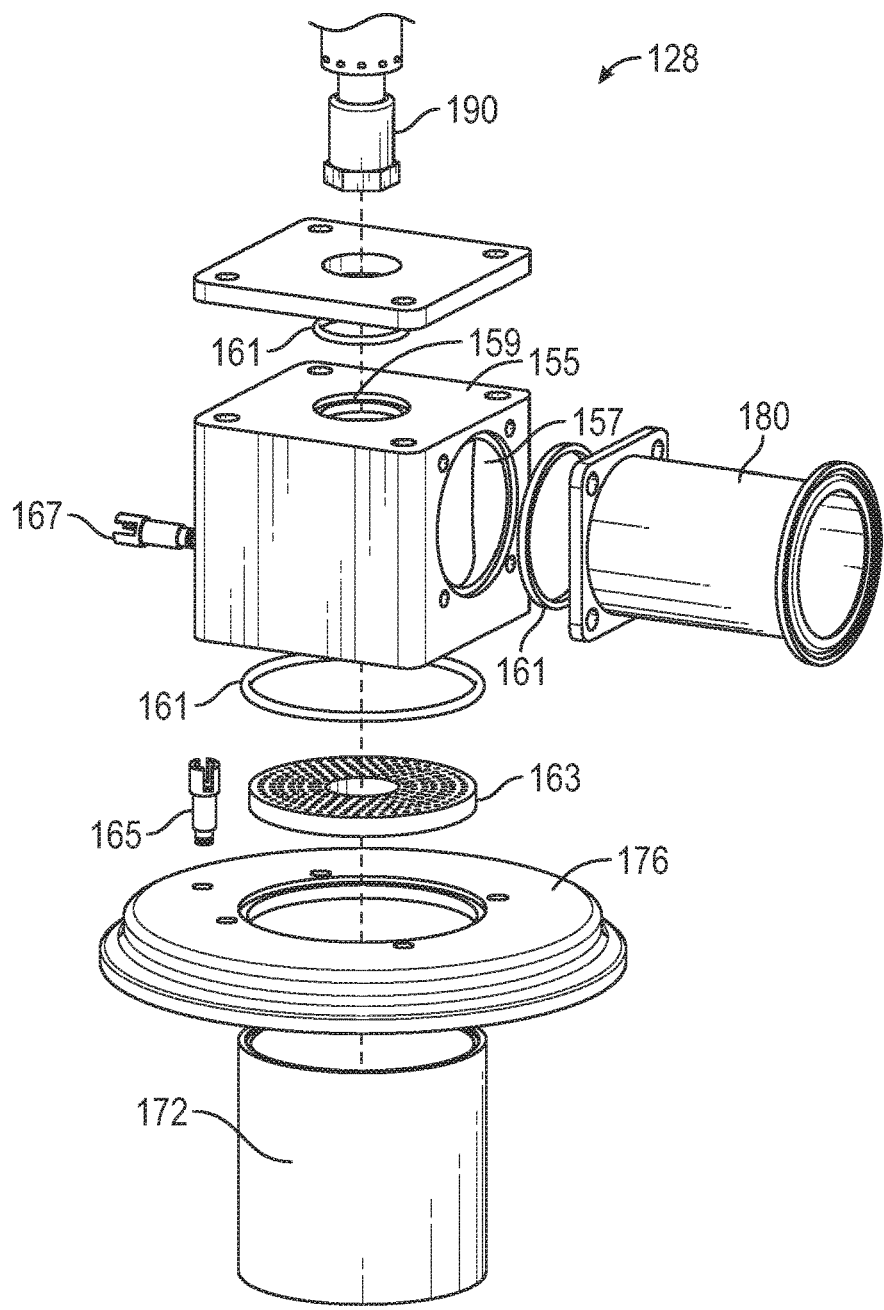
FIG. 6 is an exploded view of a gas inlet manifold.
Figure 7:
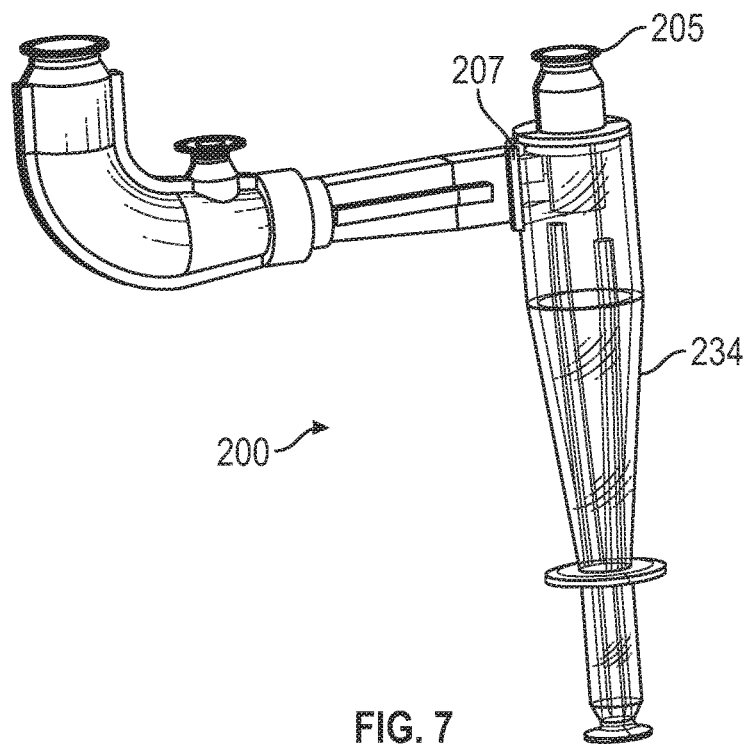
FIG. 7 is an outlet manifold of a spray drying system.

Referring now to FIGS. 4 and 5, a cross-sectional view of an assembled gas inlet manifold 28, atomizer 14, and inlet conduit 72 is shown. Gas inlet manifold 28 comprises an inlet conduit 72 and annular connector 76. Annular connector 76 is adapted to form an air-tight seal with drying chamber inlet annular connector 42. A securing mechanism (e.g., second clamp 88) can be provided to secure the respective annular connectors (76, 42) together.

Figure 8:
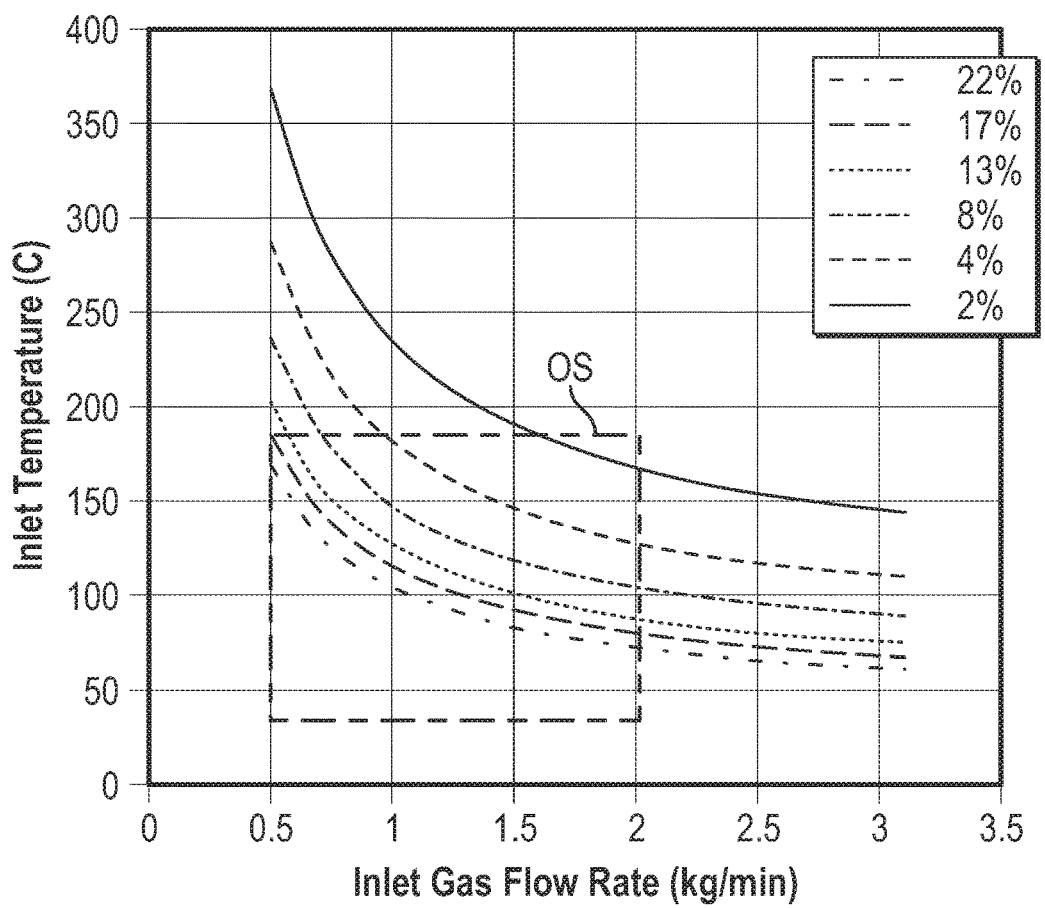
FIG. 8 is a graph showing results of relative humidity in a drying at the outlet of the drying chamber as a function of inlet gas flow rate and temperature of the drying gas at the drying chamber inlet.

In some embodiments, inlet conduit 72 can extend through the opening of the drying chamber at the inlet end 30 into the interior of drying chamber 12. The extension of inlet conduit 72 into the drying chamber can reduce the exposure of inner walls of the drying chamber at the inlet end 30 to heat from the drying gas entering the drying chamber. Alternatively, the outlet of inlet conduit can be flush with the opening into the drying chamber or positioned outside of the drying chamber.

Referring to FIGS. 4 and 5, a spray liquid inlet pipe 90 defines a spray liquid passageway. Spray liquid inlet pipe 90 has a proximal end coupled to reservoir 16 (FIG. 1), or coupled to an intermediate conduit member that is, in turn, fluidly coupled to reservoir 16. Spray liquid inlet pipe 90 has a distal end 92 that extends to atomizer 14. In some embodiments, the spray liquid inlet pipe extends through at least a portion of the gas passageway as shown in FIGS. 4 and 5. An opening 94 can be provide in drying gas conduit 80, through which spray liquid inlet pipe 90 can pass.

As shown in FIGS. 4 and 5, in some embodiments spray liquid inlet pipe 90 can be centrally located within at least a portion of drying gas conduit 80. In particular, spray liquid inlet pipe 90 can be positioned centrally within the drying gas conduit 80 at a portion adjacent to, and/or extending into, drying chamber 12.

FIG. 6 illustrates another embodiment of a gas inlet manifold 128. Gas inlet manifold 128 can comprise an annular flange 176, an inlet conduit 172, and a coupling member 155. Coupling member 155 comprises a first opening 157 for receiving a drying gas through a drying gas conduit 180 and a second opening 159 for receiving a spray liquid inlet pipe 190. Inlet conduit 172 can extend downward from flange 176 to extend into drying chamber when gas inlet manifold 128 is coupled to the drying chamber.

One or more securing mechanisms (such as O-ring members 161) can be provided to secure drying gas conduit 180 and spray liquid inlet pipe 190 to coupling member 155 in an airtight manner.

In some embodiments, gas inlet manifold 128 can comprise one or more gas dispersers 163 to reduce turbulence and/or redirect air flow from drying gas conduit 180 in a desired manner. In some embodiment, one or more pressure taps 165 can be provided at portions along the gas or spray liquid conduits.

In addition, one or more temperature sensors (e.g., disposable temperature sensor 167) can be provided to determine a temperature of the drying gas at one or more locations within drying gas conduit 180, coupling member 155, inlet conduit 172, and/or drying chamber 12.

FIG. 7 illustrates an exemplary outlet manifold 200 for use with a spraying drying apparatus. Outlet manifold can comprise a coupling member 205 for connecting to an opening at outlet end 32 of drying chamber 12. Outlet manifold 200 further comprises a rigid collection cone 234 and an outlet 207 to exhaust drying gas exiting the drying chamber.

For spray drying applications, it can be desirable to minimize residual moisture content for the powder produced, while maintaining a desirable product throughput (thereby lowering the size of the dryer and usage of nitrogen). To achieve a lower moisture content, one can increase the drying capacity of the dryer by either increasing the inlet temperature or increasing the inlet gas flow rate. FIG. 8 is a graph showing results of relative humidity of a drying gas as it exits at the outlet of the drying chamber as a function of inlet gas flow rate and temperature of the drying gas at the drying chamber inlet.

In some embodiments, the preferred operating space is within boundary OS shown in FIG. 8. Thus, for example, in a preferred embodiment a flow rate of the drying gas can be between 0.5 and 2 kg/min and inlet temperatures can be between 25° C. and 175° C. The following table reflects preferred ranges of flow rates and temperatures for certain embodiments reflected in FIG. 8.

| Outlet RH | Inlet Temperature Range (° C.) | Inlet Gas Flow Rate (kg/min) |
|---|---|---|
| 2% | 160-185 | 1.7 to 2.0 |
| 4% | 125-185 | 1.0 to 2.0 |
| 8% | 100-185 | 0.7 to 2.0 |
| 13% | 80-175 | 0.6 to 2.0 |
| 17% | 75-170 | 0.55 to 2.0 |
| 22% | 70-165 | 0.5 to 2.0 |

Exemplary Spacing Members and Spacing Member Geometry

Additional examples and technical details of suitable spacing members (e.g., heat shield members) for use with the systems and methods described herein are set out below.

The heat shield can be configured to provide a desired isolation of the heat sensitive drying chamber material from the hot inlet gas. Structures and considerations of the heat shield can include: an inlet gas flow director, a spacing member between the inlet gas piping and the heat sensitive chamber connection, and the location of the atomizing nozzle.

The inlet gas flow director can be configured to introduce a hot inlet gas into the drying chamber at a sufficiently far distance from the drying chamber walls such that the drying chamber walls do not interact with the hot drying gas prior to contact by the gas with the atomized liquid from the nozzle. The atomized liquid from the nozzle can be evaporated by the drying gas in a relatively small volume around the spray plume, thereby reducing the temperature of the atomizing gas to an outlet temperature of the drying chamber, or a temperature that is substantially similar to that temperature (e.g., +10 degrees C.). In some embodiments, the drying chamber material is selected to withstand at least a temperature of the gas at the outlet (e.g., the outlet temperature).

A gas inlet pipe can, in some embodiments, extend into the drying chamber to reduce the likelihood of high temperature inlet gases contacting side walls of the drying chamber before being cooled by contact with atomized liquid. The amount that the flow directed (e.g., gas inlet pipe) extends into the drying chamber can be varied to account for flow rates, gas turbulence, and atomizer location in specific drying chamber geometry and spraying conditions.

For example, a pipe extending between 2 and 6 inches, or 3 and 5 inches, or 3.5 to 4.5 inches, or 4 inches, into a drying chamber can direct the flow of gas reliably into the chamber, thereby reducing the likelihood of drying gas reaching the chamber wall before evaporative cooling has occurred.

The location of the liquid atomizer is preferably selected such that the heated drying gas exiting the inlet flow director contacts the atomized liquid stream exiting the nozzle prior to contacting the walls of the chamber. A liquid atomizer located axially in the center of the inlet flow director and extending for example, less than 3 inches, less than 2 inches, less than 1.5 inches, or, more preferably between about 0.5 and 1.5 inches (e.g., 1 inch), past the end of the inlet pipe can accomplish the desired cooling effect. In some embodiments, different location of the nozzle may be possible, however, so long as the hot inlet gas is contacted with the atomized liquid prior to the hot inlet gas interacting with the chamber walls. In general, however, locating the atomizer close to the outlet of the gas inlet pipe (e.g., the inlet gas flow director outlet) is preferred.

A spacing member can prevent exposure of the drying chamber attachment point to hot inlet gas temperatures by conduction of heat from the inlet gas flow director into the drying chamber attachment point. The spacing member is preferably configured so that the surface temperature at the attachment point of the drying chamber is less than a maximum allowable drying chamber temperature. Characteristics of the spacing member that determine the temperature of the member at the drying chamber attachment point can include: the thermal conductivity of the spacing member material, the thickness of the spacing member, the diameter of the inlet gas flow director, and the distance between the inlet gas flow director and the drying chamber attachment point.

An exemplary spacer geometry is illustrated below with an annular shape; however, other geometries are possible. The material of the spacing element can be any material that is capable of withstanding the temperatures of the inlet gas, such as PEI, metal, PTFE, PVDF, PEEK, Nylon, and PPSU. In order to design the spacer to satisfy the design premises described herein, one can determine the minimum geometry constraints for the selected spacer material by approximating the spacer element as a fin with adiabatic tip condition.

FIG. 9 illustrates the exemplary assembled gas inlet manifold shown in FIG. 5, with additional dimensions r0, r1, and t (discussed below) identified. For an exemplary annular spacing member, a factor defining the heat transfer rate in the space is first calculated m=sqrt(2h/kt) where m is the heat transfer factor, h is the average convective heat transfer coefficient at the spacer surface W/m^2*K, k is the thermal conductivity of the spacer material (W/m*K), and t is the thickness of the spacer.

A characteristic length of the spacer can be determined, based on the specific geometry of the spacer selected. For an annular geometry, the characteristic length is given as Lc=pi*(r1^2−r0^2)/2*pi*(r1c^2−r0^2) where Lc is the characteristic length, r1 is the radius of the spacer element at the drying chamber connection, r0 is the diameter of the inlet drying gas flow director, and r1c is a corrected spacer element radius. The corrected spacer element radius is given as r1c=r1+t/2 where t is the thickness of the spacer element. Once the heat transfer factor is known, the geometry of the spacer element is designed such that temperature at the drying chamber attachment point is less than or equal to 1.4% above the chamber outlet temperature (in degrees K). This occurs at a characteristic length (Lc) of greater than or equal to 5/m.

Accordingly, in some embodiments, the characteristic length (Lc) of the spacer is greater than or equal to 5/m, with m being related to the convective heat transfer coefficient, the thermal conductivity of the spacer material, and the thickness of the spacer.

In one example, a spacer element was constructed of PEI with an inlet flow director diameter of 3", a spacer diameter of 6", and a spacer thickness of 0.25". The average convective heat transfer coefficient was estimated to be 60 W/m^2/K, and the thermal conductivity of PEI was assumed to be 0.22 W/m*K. Using the previously disclosed method, the minimum characteristic length was determined to be 0.017 m, and the actual constructed and tested length was 0.449 m. This spacer successfully protected the drying chamber from inlet gas temperatures as high at 190° C.

In another example, a spacer element was constructed of 304 stainless steel with an inlet flow director diameter of 3", a spacer diameter of 6", and a spacer thickness of 0.1". The average convective heat transfer coefficient was estimated to be 60 W/m^2/K, and the thermal conductivity of 304 stainless steel was assumed to be 16 W/m*K. The minimum characteristic length in this case was determined to be 0.092 m and the actual constructed and tested length was 0.479 m. This spacer geometry also successfully protected the drying chamber for inlet gas temperatures of 190 C.

TABLE 1 below shows a comparison of the results of example 1 and example 2.

|  | Material | Thermal Conductivity (W/m*K) | Minimum Lc | Constructed Values | | | Actual Lc (m) |
|---|---|---|---|---|---|---|---|
|  |  |  |  | r0 (m) | r1 (m) | t (m) |  |
| Example 1 | PEI | 0.22 | 0.017 | 0.0381 | 0.0762 | 0.00635 | 0.449 |
| Example 2 | 304 Stainless Steel | 16 | 0.092 | 0.0381 | 0.0762 | 0.00254 | 0.479 |

Exemplary Operating Space

Figure 10:
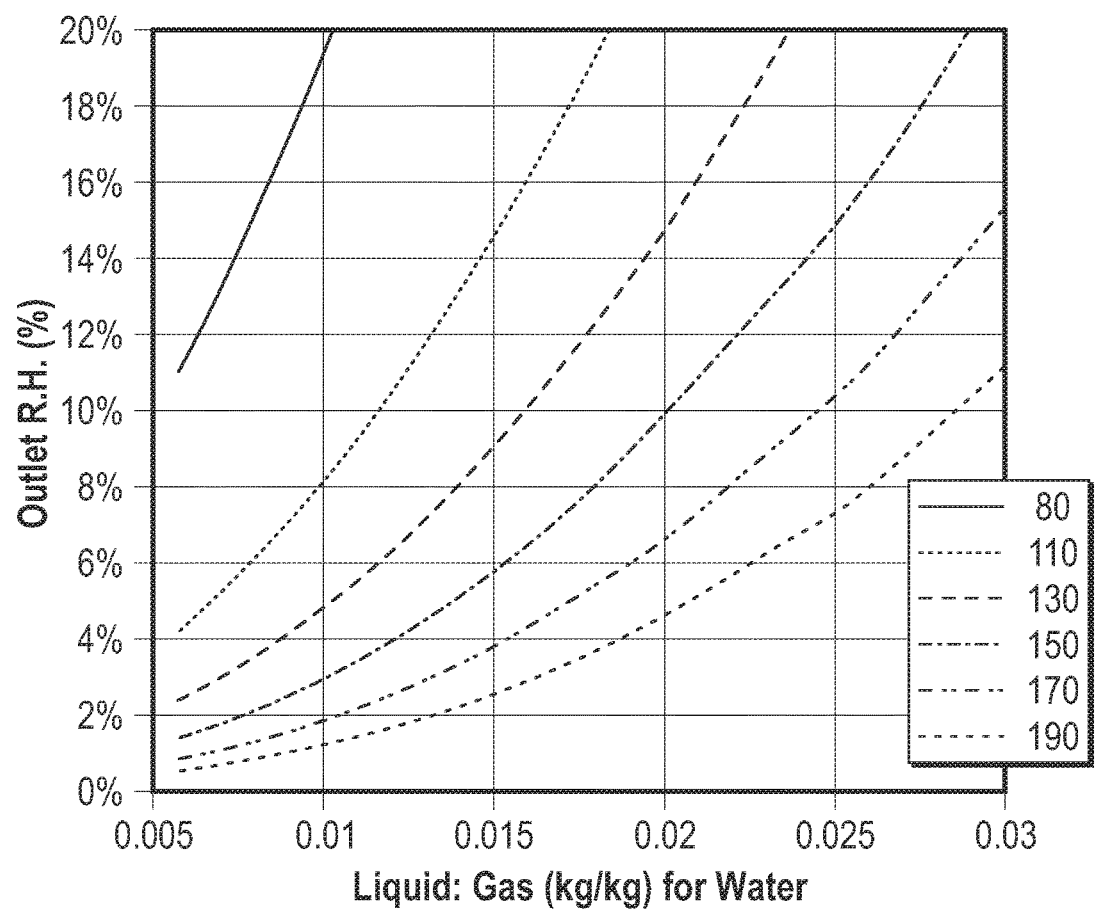
FIG. 10 depicts an exemplary thermodynamic operating space for a single-use dryer.
Figure 11:
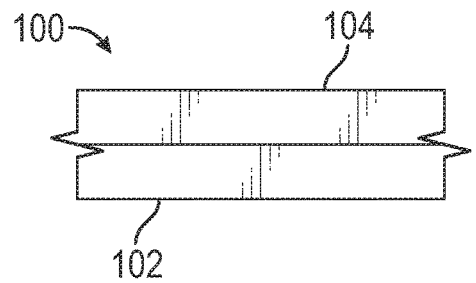
FIG. 11 illustrates a schematic view of a portion of a drying chamber with a plurality of layers.
Figure 12:
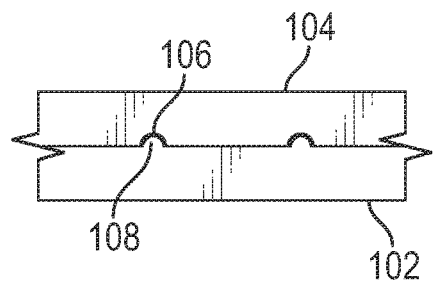
FIG. 12 illustrates another schematic view of a portion of a drying chamber with a plurality of layers.

As discussed above, the spacing members (e.g., heat shield members) disclosed herein can protect the temperature-sensitive drying chamber material from high inlet temperatures that provide improvements in producing dry powders with industrially viable throughput. In addition, the dryness of heat labile compounds (for example, proteins) can be an important determiner of stability of quality of the final powder. FIG. 10 depicts an exemplary thermodynamic operating space for a single-use dryer spraying water.

The liquid (and therefore powder) throughput of the dryer can be determined by the amount of heated gas required to vaporize the atomized liquid stream, or liquid to gas ratio (kg/kg). For a chamber made from a heat sensitive material, for example LDPE, without a mechanism to shield the bag from the inlet temperatures, the maximum allowable inlet temperature is 100° C. At temperatures higher than 100° C., the integrity of the drying chamber (e.g., bag) can be in jeopardy due to melting.

FIG. 10 illustrates that even for very small liquid to gas ratios (e.g., very low throughput), the driest powder that can be produced is around 6% residual water (assuming equilibrium with the outlet relative humidity). This would produce a severely limited operating space, or even eliminate the ability to manufacture certain products on the dryer if very low residual water is required.

Installation of a spacing member, such as the inlet heat shields described herein, allows significantly higher inlet temperatures to be achieved with the same chamber material. For example, in one embodiment, the inlet temperature can be less than 250° C. In other embodiments, the inlet temperature can be between 100° C. and 200° C.

In other embodiments, the inlet temperature can be between 100° C. and 250° C., or between 100° ° C. and 200° C. for a drying chamber constructed of LDPE. As shown in FIG. 10, production of very dry powders at favorable throughputs can be achieved when inlet temperatures exceed 110° C., exceed 130° C., and more preferably, exceed 150° C. In each case, the upper temperature boundary can be 250° C. or, alternatively, 200° C.

As such, the spacing member allows a heat-sensitive material to be used with a single-use drying chamber in an operating space with similar operating conditions to a non-heat sensitive dryer of the same size (for example, one made from stainless steel).

In one example, a liquid stream containing 7 wt % of 80:20 trehalose:leucine (with ($H_2O$ as solvent) was sprayed on a single-use dryer with LDPE chamber and spacing member installed on the inlet at a liquid to gas ratio of 0.014 (wt/wt). The outlet relative humidity at this condition was 6% for an inlet temperature of 150° C., producing an outlet temperature of 70° C.

In another example, the same liquid stream was sprayed at a liquid to gas ratio of 0.024 (wt/wt). The outlet relative humidity at this condition was 7% for an inlet temperature of 185° C., producing an outlet temperature of 78° C.

In some embodiments, the systems and methods disclosed herein can operate at a temperature between 130° C.-190° C., or between 150° C. and 190° C. Thus, the operating space in this range can be bounded by the respective temperature lines illustrated in FIG. 10.

In other embodiments, the systems and methods disclosed herein can operate at a temperature between 130° C.-190° C., or between 150° C. and 190° C., with a product that has an outlet relative humidity less than 12%, less than 10%, or between 2% and 10%. Thus, the operating space in this range is bounded by both the respective temperature lines and the respective ranges of outlet relative humidity.

In other embodiments, the systems and methods disclosed herein can operate at a temperature between 130° C.-190° C., or between 150° C. and 190° C., and at a liquid to gas ratio that is between 0.015 and 0.03. Thus, the operating space in this range is bounded by both the respective temperature lines and the respective ranges of liquid to gas ratios.

Spray Drying Chambers with Multiple Layers

As discussed above, the single-use drying chamber can be formed of a single material or can comprise an inner layer and one or more outer layers.

FIG. 11 illustrates a schematic of an embodiment of a single-use spray drying chamber 100 that includes an inner layer 102 and an outer layer 104. As discussed above, inner layer 102 can be formed of any material suitable to completely contain the product, and outer layer 104 can be formed of various disposable or reuseable materials.

In one embodiment, outer layer 104 can be a conventional drying chamber (e.g., a stainless steel drying chamber) and the inner layer 102 can be flexible material that is positioned within outer layer 104. In some embodiments, the inner layer 102 can comprise a flexible material that is positioned within the outer layer and inflated to contact the outer layer, thereby providing a sterile containment structure.

In another embodiment, outer layer 104 can comprise a flexible layer that at least partially surrounds inner layer 102. Some exemplary materials for the outer layer include stainless steel, nylon, HDPE, PET, BoPET, PETE, Polystyrene, PVC, PES, PSU, PC, PA, PBT, and LDPE. In some embodiments, inner layer 102 is formed of a material that is vulnerable to the operating pressure of the system and outer layer 104 is selected to provide additional structure to withstand the operating pressure of the system.

If multiple layers are provided, the inner layer can be secured or unsecured to the adjacent outer layer. The layers can be secured in various manners. For example, as shown in FIG. 12, one or more engaging members 106, 108 can be provided in an outer surface of inner layer 102 to engage with an inner surface of outer layer 104. The engaging members can be mating components (such as mating tabs/ notches or mating bumps/recesses) that permit engagement between facing surfaces of two layers.

Alternatively, at least some portions of the facing surfaces of the inner and outer layers can be adhered to one another. For example, in one embodiment, outer layer 104 can comprise one or more laminate layers that are secured to at least some portions of the inner layer to provide structural rigidity.

In embodiments where inner layer 102 is a flexible material that is inflated to define an internal volume of the drying chamber, inner layer 102 can be sized slightly larger than outer layer 104 so that, upon inflation, it fully engages with the inner surface of outer layer 104. For example, the inner layer can be expandable from a collapsed configuration to a fully-expanded configuration and the inner layer can have a first diameter in the fully-expanded configuration taken at a midpoint between the inlet end and the outlet end. The first diameter can be sized larger than a second diameter of the outer layer, taken at a midpoint between the inlet end and the outlet end of the outer layer.

Figure 13:
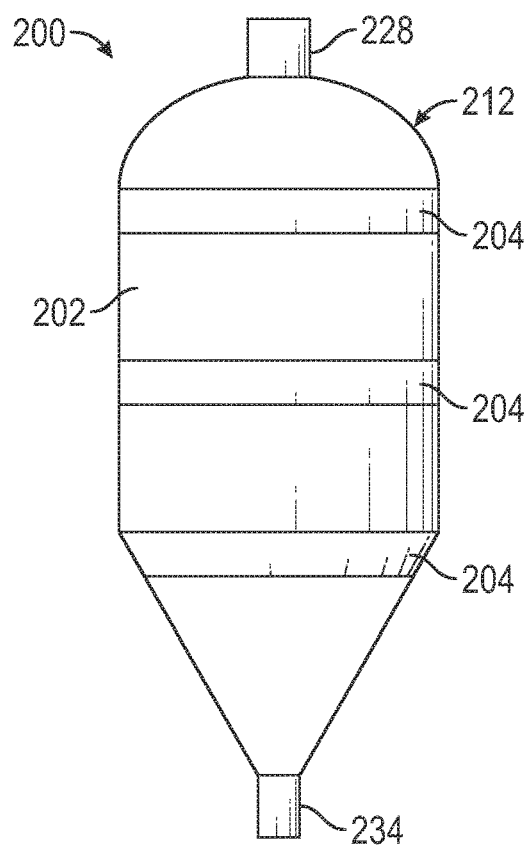
FIG. 13 illustrates another schematic of a drying chamber with an outer layer that partially surrounds an inner layer.

As discussed above, in embodiments with multiple layers, the outer layer can completely surround the inner layer or the outer layer can partially surround the inner layer. FIG. 13 illustrates a spray drying system 200 in which a single-use drying chamber 212 has one or more outer layers 204 that partially surround an inner layer 202. In FIG. 13, outer layer 204 is illustrated as a plurality of bands or strips of material that provide additional structural rigidity to inner layer 202; however, it should be understood that other shapes and arrangements of one or more partially-surrounding outer layers can be used.

Sterilization of Single-Use Drying Chambers

The disposable portions of the single-use drying chambers disclosed herein (e.g., a single layer or an inner layer of a multi-layer drying chamber) can be sterilized prior to use and packaged for sterile delivery to the location of the spray drying system. In one embodiment, the single-use drying chambers can be subjected to gamma irradiation sterilization prior to use.

Gamma irradiation sterilization involves exposing the single-use drying chambers to radionuclide elements (e.g., Cobalt 60) that emit gamma rays during radioactive decay. Unlike heat sterilization which can damage some of the materials disclosed herein, gamma irradiation sterilization does not cause heat stress.

Accordingly, in one embodiment, a manufacturing method of a single-use drying chamber can include exposing the single-use drying chamber to gamma irradiation to sterilize the single-use drying chamber and enclosing the sterilized single-use drying chamber in sterile packaging for delivery to the location of the spray drying equipment. In this manner, the single-use drying chamber is sterilized and isolated from the environment until ready for use.

As discussed above, all (or some) of the other components in the product flow path can be pre-sterilized and sterile packaged so that they are maintained in a state that is ready for use.

Spray Drying Liquids and Active Components

The liquids that are spray dried into product (e.g., powder) can vary. For example, in some embodiments, the spray liquids can comprise one or more active components, such as active pharmaceutical ingredients that exert a desired physiological effect on a mammal, including, but not limited to humans. Non-limiting examples of active ingredients according to the disclosure include but are not limited to proteins, antibodies, monoclonal antibodies (mAbs), antibody fragments, peptides, oligonucleotides, non-mAb proteins, small molecules, high potency small molecules, antibody-drug conjugates, live microbials, vaccines, and various derivatives of such materials.

Other components can be used in the spray liquids of the systems and processes described herein to produce different products, including product that does not contain active pharmaceutical ingredients. For example, spray liquids can comprise a food component (e.g., milk), nutritional components (e.g., fat soluble vitamins), or various process intermediates (e.g., cell culture media, bulk protein intermediates, and chemical intermediates).

By using the single-use components described herein, a number of advantages are possible. For example, the materials of the single-use components described herein are readily sterilized, cost-effective, and lightweight for quick changeovers between different spray drying processes. For example, a single-use drying chamber can be used in a first spray drying process with a first spray liquid, then replaced with a second inner surface for use in a second spray drying process with a second (different) spray liquid.

When an inner layer is used within a reusable container (e.g., a stainless steel drying chamber), the inner layer can be removed from the stainless steel drying chamber and replaced with another inner layer. When the inner layer is the only layer or when it is used inside another layer (e.g., a flexible and/or disposable material), replacement of the inner layer includes removing the inner layer and securing a different inner layer to the system.

Removal and replacement can be performed during product changeovers (e.g., when the second spray liquid is different from the first spray liquid), after a predetermined number of spray drying operations with the first inner surface, or after a predetermined amount of time of spray drying operations. The act of replacing the first inner surface with a second inner surface can therefore be performed in lieu of sterilizing and reusing the drying chamber.

In certain embodiments, the spray drying process may provide one or more of the following advantages: aseptic processing capable of supporting current final formulation trends for biologics; continuous final drug product processing as part of a continuous, agile, low-volume clinical supply train; multiple products to be processed in the same processing suite; vastly reduced processing time and cleaning requirements compared to aseptic spray drying or lyophilization and high potency processing; and significantly reduced equipment and operational costs.

In view of the many possible embodiments to which the principles of the disclosure may be applied, it should be recognized that the illustrated embodiments are only preferred examples and should not be taken as limiting the scope of the claims. Rather the scope of the claimed subject matter is defined by the following claims and their equivalents.

The invention claimed is:

1. A spray-drying apparatus, comprising:
 a gas inlet manifold comprising an inlet conduit that defines a gas passageway and a spacing member that extends laterally from the gas passageway of the gas inlet manifold;
 a single-use drying chamber having a first opening defined by a first surface portion at an inlet end, a second opening defined by a second surface portion at an outlet end, and a third surface portion extending longitudinally from the inlet end to the outlet end;
 a spray liquid inlet pipe having a proximal end and a distal end, the distal end of the spray liquid inlet pipe being coaxial with the inlet conduit; and an atomizer at the distal end of the spray liquid inlet pipe, the atomizer extending past an outlet end of the inlet conduit, wherein the first surface portion is coupled to the spacing member at a location that is spaced apart from the gas passageway by a distance greater than 50% of a radius of the gas passageway to establish a gap between the first surface portion and an outside surface of the inlet conduit, and wherein the single-use drying chamber has an inner surface that is formed of a polymeric material.

2. The apparatus of claim 1, wherein the first surface portion is spaced apart from the gas passageway by a distance greater than 75% of the radius of the gas passageway.

3. The apparatus of claim 1, wherein the first surface portion is spaced apart from the gas passageway by a distance greater than 100% of the radius of the gas passageway.

4. The apparatus of claim 1, wherein the first surface portion is spaced apart from the gas passageway by a distance greater than 125% of the radius of the gas passageway.

5. The apparatus of claim 1, further comprising a heater configured to supply a heated drying gas at a temperature greater than 100° C., greater than 150° C., or greater than 200° C.

6. The apparatus of claim 1, wherein the polymeric material is a thermoplastic material.

7. The apparatus of claim 1, wherein the spray liquid inlet pipe extends through at least a portion of the gas passageway.

8. The apparatus of claim 1, wherein the distal end of the spray liquid inlet pipe extends into the single-use drying chamber.

9. The apparatus of claim 1, wherein the single-use drying chamber comprises:

a first layer; and a second layer that at least partially surrounds the first layer.

10. The apparatus of claim 9, wherein the first layer is formed from a flexible material that can inflate from a collapsed configuration to a fully-expanded configuration, wherein the first layer has a first diameter in the expanded configuration taken at a midpoint between the inlet end and the outlet end, and the second layer has a second diameter at a midpoint between the inlet end and the outlet end, and wherein the first diameter is larger than the second diameter.

* * * * *